Jan. 5, 1954 W. E. LAMMERTS Plant Pat. 1,238
LILAC PLANT
Filed July 11, 1952 2 Sheets-Sheet 1
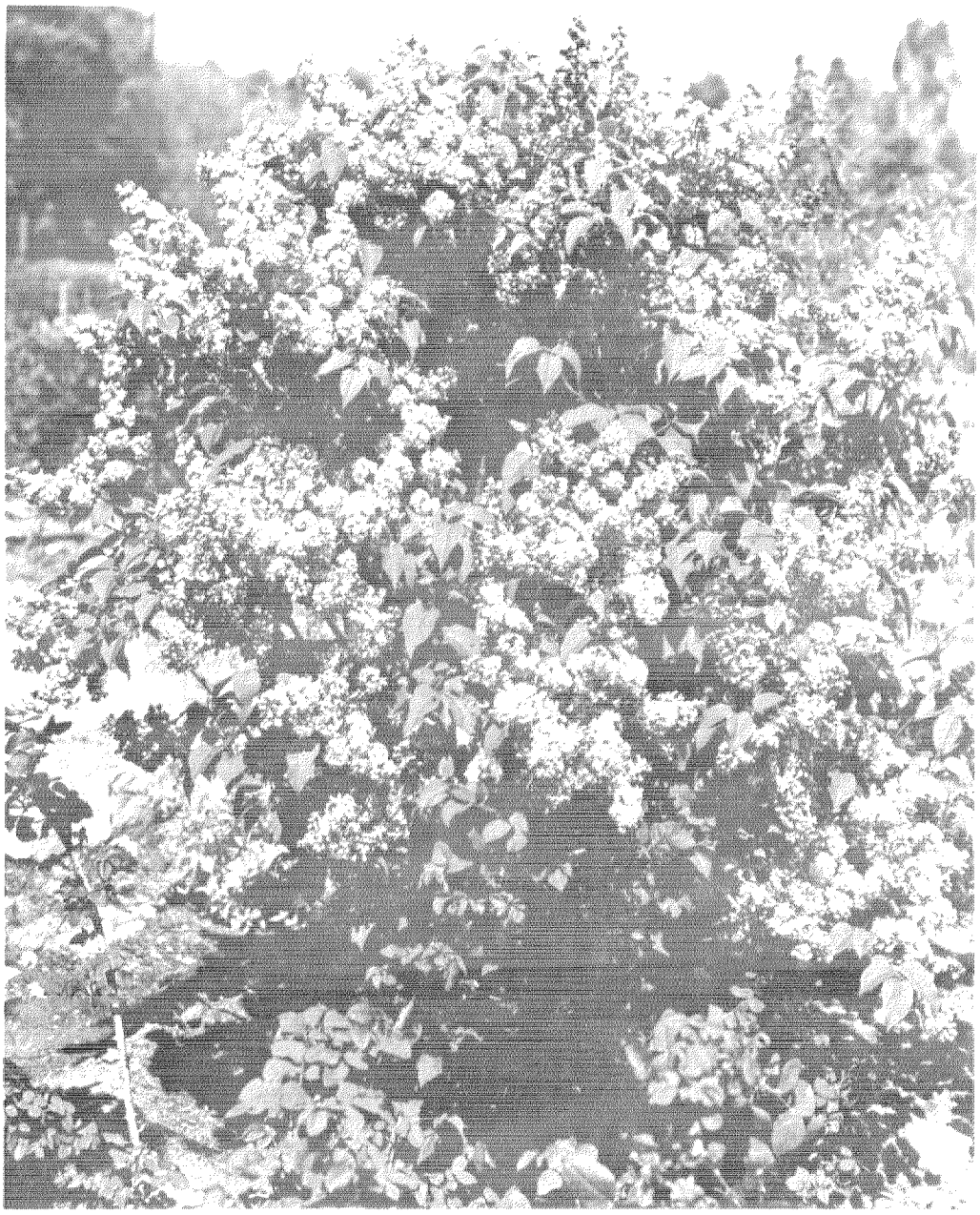
Inventor
W. E. Lammerts
By: Robert Cobb
Attorneys.

Jan. 5, 1954 W. E. LAMMERTS Plant Pat. 1,238
LILAC PLANT
Filed July 11, 1952 2 Sheets-Sheet 2
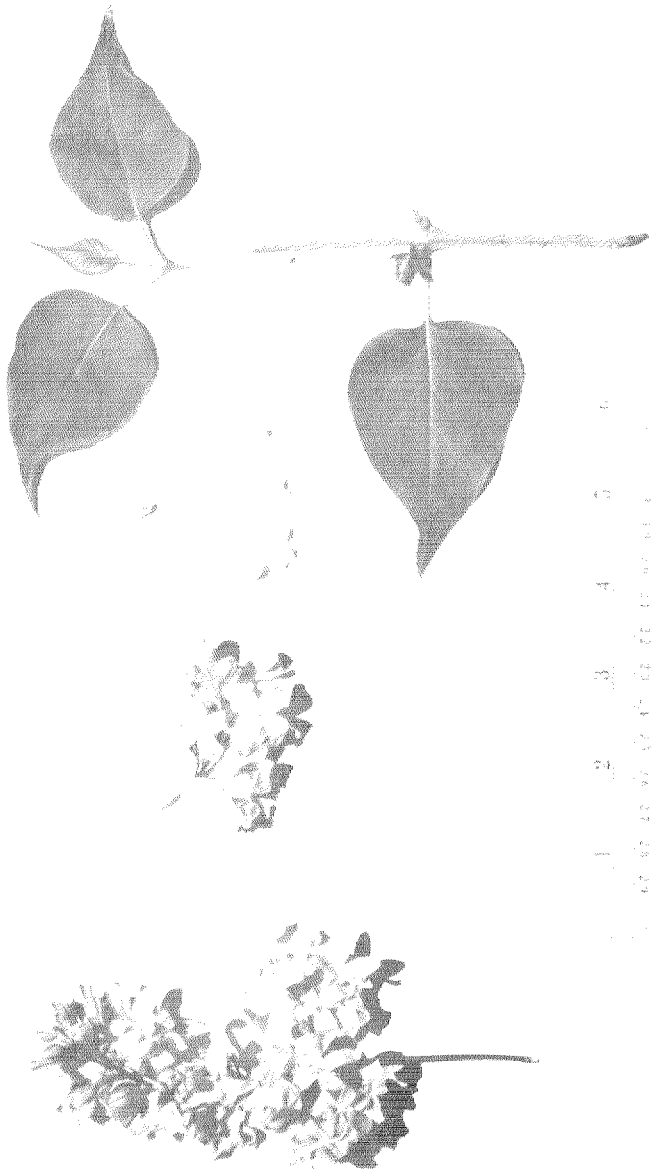
Inventor
W. E. Lammerts
By Cobb & Cobb
Attorneys Patented Jan. 5, 1954 Plant Pat. 1,238

UNITED STATES PATENT OFFICE 1,238

LILAC PLANT

Walter E. Lammerts, La Canada, Calif., assignor to Descanso Distributors, Inc., La Canada, Calif., a corporation of California Application July 11, 1952, Serial No. 298,477

1 Claim. (Cl. 47—60)

The present invention relates to a new and distinct variety of lilac plant originated by me by crossing two unnamed and unpatented seedlings, each of which was originated from seed of an unnamed and unpatented early-leafing variety identified in my breeding records by the identification number C112.

The primary objective in making this cross was to produce an improved variety of lilac which would flower normally in southern California and comparable climatic areas where the winter seasons are comparatively short and mild. Most lilacs, including the usual eastern lilacs, require more winter-chilling than can be obtained in southern California and comparable areas, with the result that these prior lilacs do not bloom satisfactorily in these latter areas, and are unable to produce more than sporadic and very small flower clusters.

My principal objective above referred to has been fully achieved by the new variety which I have produced from the aforementioned breeding, and in addition to requiring less than normal winter-chilling, with resultant normal flowering in spite of the warmest winter seasons in southern California and comparable climates, my new variety is further characterized by its regularity and abundance of production of very large flower clusters measuring from 7 to 9 inches in length and from 7 to 10 inches in width, such clusters being composed of relatively large florets measuring from ⅞ of an inch to 1⅛ inches in diameter. Occasionally, the flower clusters will be as large as 12 inches in both length and width.

My new variety is still further characterized by the fact that the flowers are borne on plants of exceptionally vigorous growth, and the plants are well-clothed with fine, large foliage.

In respect to the color of its flowers, my new variety bears flowers which are substantially identical in color to several varieties, such as the well-known variety "Kate Sessions" (unpatented), but these other varieties do not do well in southern California and in similar mild climates, and although the variety "Kate Sessions" usually blooms regularly in mild climates, the blooms are comparatively small under such climatic conditions, with the clusters measuring only about 4½ inches in length and from five inches to 6 inches in width, with the individual florets measuring only from about ¾ of an inch to ⅞ of an inch in diameter.

It will thus be understood from the foregoing that my new variety of lilac is much superior to its parents, as well as to all other varieties of its class, particularly for climates like that which prevails in southern California.

Asexual reproduction of my new variety by cuttings and also by budding into privet understock at La Canada, California, shows that the foregoing characteristics and distinctions come true to form and are established and transmitted through succeeding propagations.

In the accompanying drawings, one drawing shows a typical specimen plant of my new variety as depicted in color as nearly true to life as it is reasonably possible to make the same in a color illustration of this character, and the other drawing shows in black-and-white the details of typical specimens of the foliage, stems, flower clusters, sub-clusters and individual florets in different stages of development.

The following is a detailed description of my new variety as observed at La Canada, California, with color terminology in accordance with Robert F. Wilson's Horticultural Colour Chart, except where general color terms of ordinary dictionary significance are obvious:

Parentage: Seedling.

*Seed parent.*—An unnamed seedling of an unnamed early-leafing variety identified as C112.

*Pollen parent.*—Another unnamed seedling of the early-leafing variety identified as C112.

Blooming habit: Early; usually from about March 25th to April 20th in southern California; in full flower and leaf about April 2nd.

Bud: Individual florets of cluster.

*Size.*—Large.

*Form.*—Short, with flat top; globular-elongate.

*Sepals.*—Smooth edge. Color—Pansy Violet, Plate 033/2.

*Calyx.*—Consisting of 4 very small lobes, each about $\frac{1}{32}$ inch long and about $\frac{1}{32}$ inch wide; calyx tube about $\frac{1}{16}$ inch wide and about ⅛ inch long.

Bloom: Individual florets of cluster.

*Size, when fully open.*—Large; length from calyx tube to center of open floret is about ⅜ of an inch; corolla tube about $\frac{1}{16}$ of an inch wide at base, and about ⅛ of an inch wide at top; florets about ⅞ of an inch to about 1⅛ inches in diameter; corolla lobes about ¼ of an inch to $\frac{5}{16}$ of an inch in width.

*Florets borne.*—In large clusters, usually measuring from 7 inches to 9 inches in length and from 7 inches to 10 inches in width; clusters consist of many florets arranged in smaller sub-clusters of several to many florets, thus giving very full, well-rounded appearance.

*Form.*—The individual florets when first open are flat until several days old; then become curled down to about the middle of the corolla lobe.

*Petalage.*—Single.

*Color.*—Center near Pastel Lilac, Plate 437; area near midrib Mauvette, Plate 537; color is substantially identical to flowers of the variety "Kate Sessions."

Petals: Thick; soft; inside and outside satiny.

*Shape.*—Elongate-rounded.

*Lasting quality.*—On plant—from 5 to 7 days. As cut flowers—from 3 to 4 days.

*Genital organs*

Stamens, anthers: Medium size; usually only two in number.

*Color.*—Light yellow; substantially identical to those of the variety "Kate Sessions."

*Arrangement.*—Typical of all single lilacs.

Stamens, filaments: Medium length. Color—substantially identical to those of the variety "Kate Sessions."

Pollen: Color—Buff yellow; substantially identical to that of "Kate Sessions."

Styles: One style of two stigmas $\frac{1}{16}$ of an inch long; style and stigmas are ¼ of an inch long. Color—very light pale yellowish-green.

Ovaries: All enclosed in calyx.

*Fruit*

Fertility: Variety is fertile with its own pollen.

Form: Elongate-capsule.

Aspect: Smooth.

Color at maturity: Brown.

Sepals: Caducous.

*Plant*

Form of plant: Bush.

Growth: Very vigorous; upright; compact.

Foliage: Size—large; leaves measure from about 2 inches to 2¼ inches wide and from about 2¾ inches to about 3¼ inches long.

*Quantity.*—Abundant.

*Color.*—New foliage: Spinach Green, Plate 0960/1; old foliage: near Spinach Green, Plate 0960/1.

*Shape.*—Ovate-pointed.

*Texture.*—Upper side—smooth; dull; somewhat velvety; flat; veins slightly indented. Under side—smooth.

*Veins.*—Quite prominent on under side.

*Edge.*—Smooth.

Wood:

*New wood.*—Color—near Willow Green, Plate 000862, tinged with brown.

*Old wood.*—Color—greyish-brown.

I claim:

A new and distinct variety of lilac plant, substantially as herein shown and described, characterized particularly as to novelty by its relatively short and mild winter-chilling requirements, by its regular and abundant production of large flower clusters consisting of large individual florets, by the substantial identify of the color of its flowers with those of the variety "Kate Sessions" (unpatented), by its vigorous habit of plant growth, and by its abundant production of large and attractive foliage.

WALTER E. LAMMERTS.

No references cited.